Figure 1D:
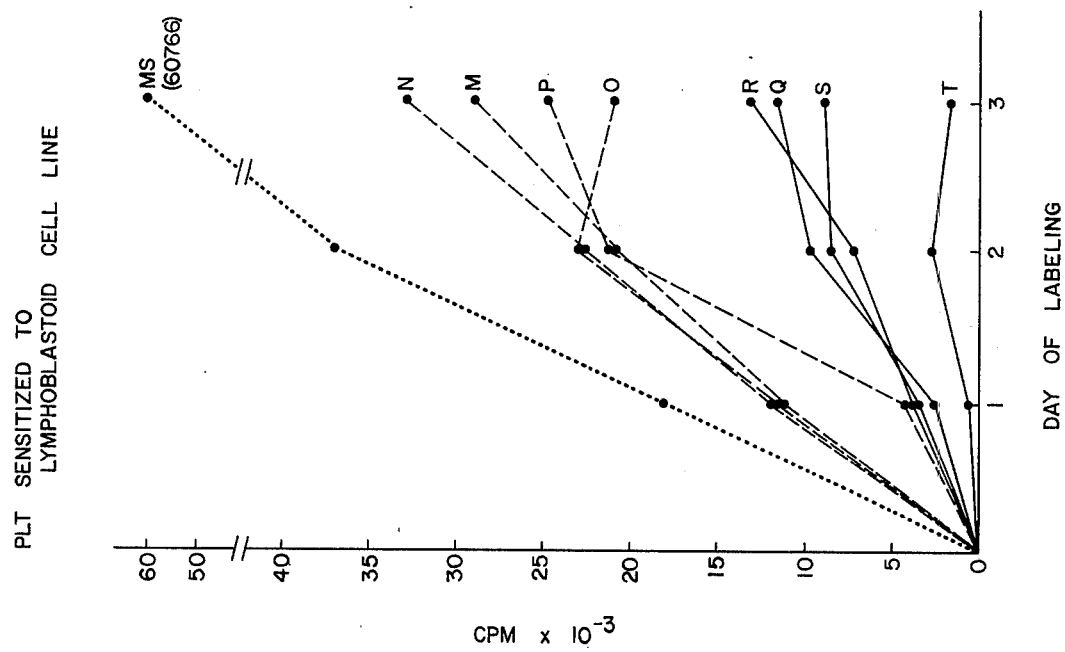

United States Patent [19]

Bach et al.

[11] 4,124,701

[45] Nov. 7, 1978

[54] METHOD FOR PREPARING A REAGENT FOR PLT AND METHOD OF USE

[75] Inventors: Marilyn L. Bach; Fritz H. Bach, both of Madison, Wis.

[73] Assignee: Wisconsin Alumni Research Foundation, Madison, Wis.

[21] Appl. No.: 814,316

[22] Filed: Jul. 11, 1977

Related U.S. Application Data

[63] Continuation of Ser. No. 697,029, Jun. 17, 1976, abandoned.

[51] Int. Cl.² .................... G01N 31/00; G01N 33/16; C12K 9/00
[52] U.S. Cl. ........................................ 424/12; 195/1.8
[58] Field of Search ............................ 195/1.8; 424/12

[56] References Cited
PUBLICATIONS

Barrett–Textbook of Immunology–2nd edition (1974) pp. 327–329.

Primary Examiner—Sam Rosen
Attorney, Agent, or Firm—Howard W. Bremer

[57] ABSTRACT

A method for preparing a reagent for primed LD typing which comprises sensitizing purified human blood leukocytes to a secondary proliferative response by incubating them, in vitro, in mixed leukocyte culture, with lymphoblastoid cell lines from homozygous typing cells, or from other cells of specified genetic type homozygous for HLA-D, or other continuous line.

9 Claims, 4 Drawing Figures

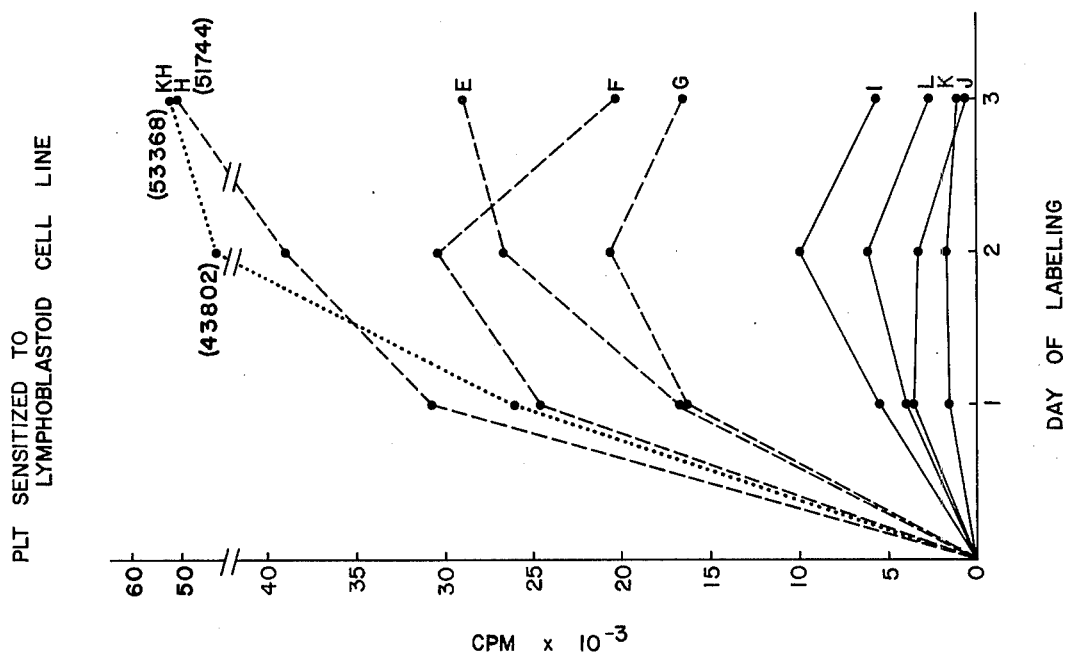
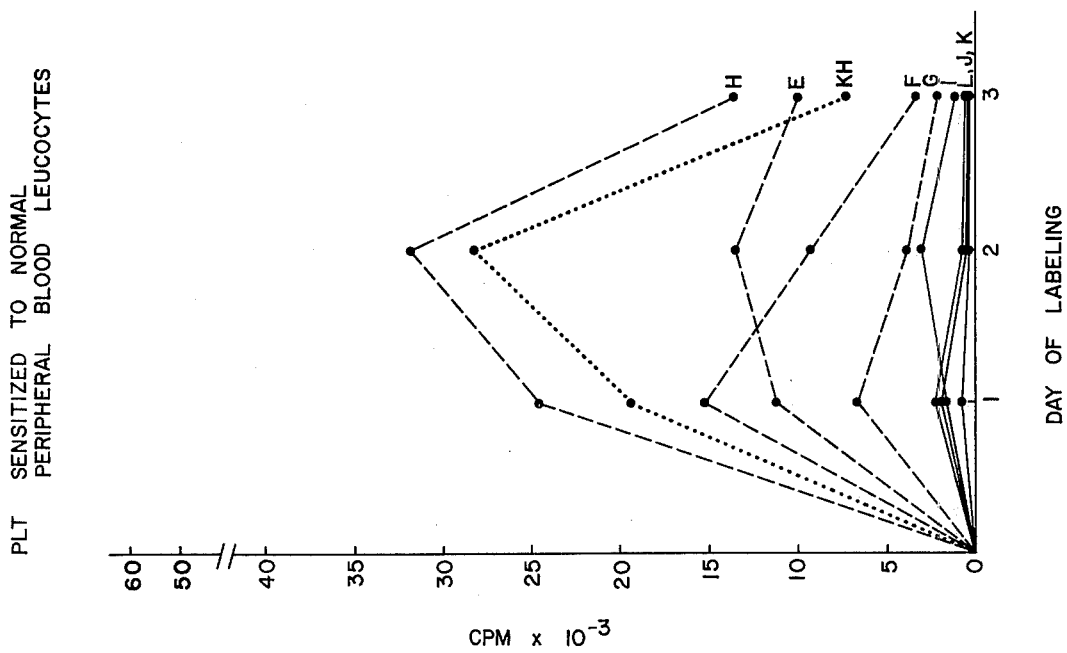

METHOD FOR PREPARING A REAGENT FOR PLT AND METHOD OF USE

The invention described herein was made in the course of work under a grant or award from the Department of Health, Education, and Welfare.

This is a continuation, of application Ser. No. 697,029, filed June 17, 1976, now abandoned.

This invention relates broadly to a method for typing or defining human leukocyte antigens.

More specifically, this invention relates to a method for preparing a reagent for typing human leukocyte antigens.

Still more specifically, this invention relates to a method for sensitizing purified human blood leukocytes for a secondary proliferative response where the sensitizing agent is a lymphoblastoid cell line from homozygous typing cells, or from other cells of specified genetic type homozygous for HLA-D, or other continuous line.

It is well known that rejection of a transplanted tissue or organ is initiated when the graft recipient's immune system recognizes genetically controlled "foreign" antigens on the grafted tissue; and that in humans a single genetic region called HLA (human leukocyte antigens) or the major histocompatibility complex (MHC), appears to control the majority of strong antigens important in graft rejections.

This invention finds particular application in the "matching" of two individuals where organ or tissue transplantation is contemplated in an effort to minimize the antigenic disparity between the donor and recipient, thereby minimizing the likelihood of rejection of the transplanted organ or tissue.

Two methods are commonly used for detecting antigens associated with the major histocompatibility complex: (i) serological testing for HLA SD (serologically defined) antigens, and (ii) mixed lymphocyte culture (MLC) tests that define disparity at an HLA LD (lymphocyte defined) locus (or at several loci). In MLC tests, lymphocytes from one individual (the "responder") are cultured for 4 to 7 days with "stimulating" lymphocytes from another individual. To prevent their proliferation, stimulating cells are treated with mitomycin C or X-rays before they are mixed. When the stimulating cells are from unrelated persons or family members whose MHC is different from that of the responder, the untreated lymphocytes proliferate; this proliferation is assayed by incorporation of tritiated thymidine or tritiated uridine into the proliferating cells. All SD and LD loci are closely linked genetically, and within families they are usually inherited as a unit called haplotype. However, since the SD and LD loci are generally separable, both the serological and MLC tests are necessary in the evaluation of the MHC relationship between two individuals.

In transplants between SD matched persons who are not related, the frequency and severity of rejection generally have been much greater than in transplants between siblings with identical MHC's; moreover, most unrelated individuals who are SD identical are LD disparate when tested by the MLC assay. There is some evidence that MLC matching for HLA LD antigens may be useful for predicting the success of a transplant.

Two major obstacles prevent the widespread use of MLC tests for transplant matching. (i) The result cannot be obtained in less than 4 to 5 days -- a time that exceeds the limits for cadaver kidney preservation. (ii) Although MLC tests can identify individuals that are matched for their LD antigens, it does not indicate which specific LD antigens the two persons bear; therefore lymphocytes from all potential donors must be tested in MLC with lymphocytes from all potential recipients.

This last problem would be alleviated by an "LD typing" method (analogous to serological typing that has been done for blood groups and HLA SD antigens) that would identify specific LD antigens. Because LD typing would preclude the necessity of the recipient and potential donor being present in the same MLC-testing laboratory at the same time, the LD type of any potential tissue donor could be determined, and the donor organ or bone marrow could be sent to an LD matched recipient at any center in the world.

A method for LD typing has been disclosed by M. J. Sheehy et al in Science, Volume 118, pp. 1308–1310, June 27, 1975, which offers a solution to these problems. Such method is based upon the earlier finding that lymphocytes stimulated to proliferation in a primary MLC exhibit an accelerated secondary proliferative response when stimulated 14 days later with leukocytes of the original sensitizing leukocyte donor (see L. C. Anderson and P. Hayry, Eur. J. Immunol. 3, 595 (1973)).

Sheehy et al (reference above) discovered not only that this process could be used for recognizing the HLA-D region antigens of the major histocompatibility complex in man, but that if the leukocytes from a person are stimulated in a primary MLC with leukocytes obtained from a second person who differs from the first person by only a single MHC haplotype, and the stimulating leukocytes are treated to prevent their proliferation in MLC, a discriminatory type of leukocyte is obtained which permits LD typing in, not only the familial, but also in the unrelated population via the secondary proliferative response method.

For example, cells (leukocytes) of individual A are "primed" by stimulating them with cells treated with mitomycin C ($B_m$ cells) obtained from a person, B, who differs from A by only a single MHC haplotype (for example, a parent or child of A). When the MLC proliferative response is essentially completed (after 9 to 14 days), the cells are used as the PLT cells. The cells remaining in the incubation medium, are recovered by centrifugation and "restimulated" with $B_m$ cells, or with cells from any other person who is to be LD typed, and their response is assayed by uptake of tritiated thymidine or tritiated uridine. On restimulation with $B_m$ cells, or with cells of family members having the same MHC that A recognized on $B_m$, a significant response, indicated by uptake of the tritiated thymidine or uridine, is observed after as few as 24 hours. Stimulation by cells of unrelated persons ranges from none to that seen with $B_m$; those persons whose cells restimulate as well as $B_m$ presumably bear LD antigens very similar to those recognized on $B_m$ by A. Thus PLT cells should identify individual bearing specific LD antigens. Many populations of PLT cells, each specific for antigens of a different LD haplotype, can easily be obtained via primary MLC's with cells from the appropriate members of different families.

It would be obvious value to have a constant and readily available source of stimulating cells for MLC sensitization that carry a known D locus determinant. Such stimulator cells could be used ultimately to sensitize responding cells that lack the determinant but have all other D determinants of the stimulating cell.

The present invention accomplishes these ends by utilizing, as the sensitizing cells in MLC, lymphoblastoid cell lines from homozygous typing cells. Thus, in accordance with the present invention, lymphoblastoid cell lines can be used for PLT priming.

The major advantage of the present invention lies in having a constant source of the same stimulus, since lymphoblastoid cell lines can be grown in any amount and appear to remain relatively constant in terms of the antigens that they express. It will be understood that other cells of specified genetic type, homozygous for HLA-D, or other continuous lines can also be used to advantage as sensitizing cells and therefore appropriate stimulating or sensitizing cells can be selected from the group.

The following reagents, media, and techniques were used in establishing the operability of the present invention as hereinafter described. It will be readily evident, however, to those skilled in the art that variations in techniques, times, volumes and types of materials and equipment and in the various media can be used without departing from the teaching and scope of the invention.

MEDIUM AND CELLS

The culture medium was RPMI 1640 with 25 mM HEPES buffer (available from Gibco Diagnostics, catalog No. 240, Madison, Wisconsin) supplemented with penicillin and streptomycin in amounts sufficient to inhibit the growth of extraneous microorganisms in the medium. Plasma pools were from at least 20 donors who had never been transfused, grafted or been pregnant. The plasma was heat inactivated (56° C for 30 minutes) before use.

Whole heparinized blood was centrifuged (15 minutes, 300 g) to obtain buffy coat cells which were further purified by the Ficoll-Hypaque Technique (Boyum, Scanad, J. of Clin. and Lab. Invest., Vol. 21, Supplement 97, pp. 1-91 (1968). Stimulating cells for primary cultures were irradiated (gamma radiation; 6000r a dose rate of about 800r/min).

METHODS

Primary Cultures

PLT cells were generated by culturing $1 \times 10^7$ responding cells which were negative for a given DW cluster with either $1 \times 10^7$ normal lymphocytes of the homozygous typing cell donor or $1 \times 10^6$ lymphoblastoid cells from that homozygous typing cell. The normal lymphocytes were irradiated (gamma radiation) to prevent their proliferation and the culturing was carried out in Falcon flasks (cat. No. 3013), in 20 ml of medium containing 5% (v/v) human plasma at 37° C. After 10 days of culturing in a 5% $CO_2$ incubator, nonadherent cells were suspended by vigorous pipetting, centrifuged (15 min., 300 g) and resuspended in fresh medium for counting. Harvested PLT cells were either restimulated or frozen in accordance with the method described below for later use.

Secondary Cultures (restimulation)

Secondary cultures were performed in microtiter plates with U or V-bottom wells. Viable PLT cells (from the primary cultures) and viable restimulating cells drawn from:
a. the original donor of the homozygous typing cell (reference restimulating cell);
b. cells of the original responding cell donor (control restimulating cells); and
c. cells from various other individuals (test restimulating cells);

($5 \times 10^4$ responding cells and $5 \times 10^4$ restimulating cells) were cultured in each well in 0.15 ml. of medium containing 25% plasma at 37° C. (The stimulating cells were not treated to prevent their proliferation). Cultures were labelled at 24, 48 and 72 hours with a $2\mu Ci$ pulse of tritiated thymidine (Nuclear Chicago, 1.9Ci/m mole) in 0.05 ml of medium and harvested 16 hours later. Cultures were harvested onto glass fiber filters and prepared for liquid scintillation counting (M. L. Bach et al, Histocompatibility Testing (1970) pp. 643-653, Munksgaard, Copenhagen).

Test cells were classified as either carrying the same HLA-D haplotype as the reference cell on the basis of genotyping wthin a family or, when test cells were used which were unrelated to the control and reference cell, by homozygrous typing cell testing.

RESULTS

FIGS. 1A and 1B show the PLT results with two different PLT cells. Results in FIG. 1A are obtained using a PLT cell in which cells of a responder that did not carry a given HLA-D cluster were sensitized to the peripheral blood lymphocytes of a homozygous typing cell donor (KH). (This homozygous typing cell does not show a significant association with the presently defined DW clusters.) The PLT cell was restimulated with the normal lymphocytes of the reference cell donor (KH), three family members carrying the same D haplotype (individuals E, F and G), a test cell from an unrelated individual carrying the same D haplotype by homozygous typing cell testing (individual H), and cells of four individuals (I, J, K and L) not carrying the D cluster by testing with the homozygous cell. The results shown in FIG. 1B are obtained using a PLT cell in which cells from a lymphoblastoid cell line from cells of KH were used for sensitization in the primary MLC. Otherwise, the resulting PLT cells were handled identically.

Figure 1C:
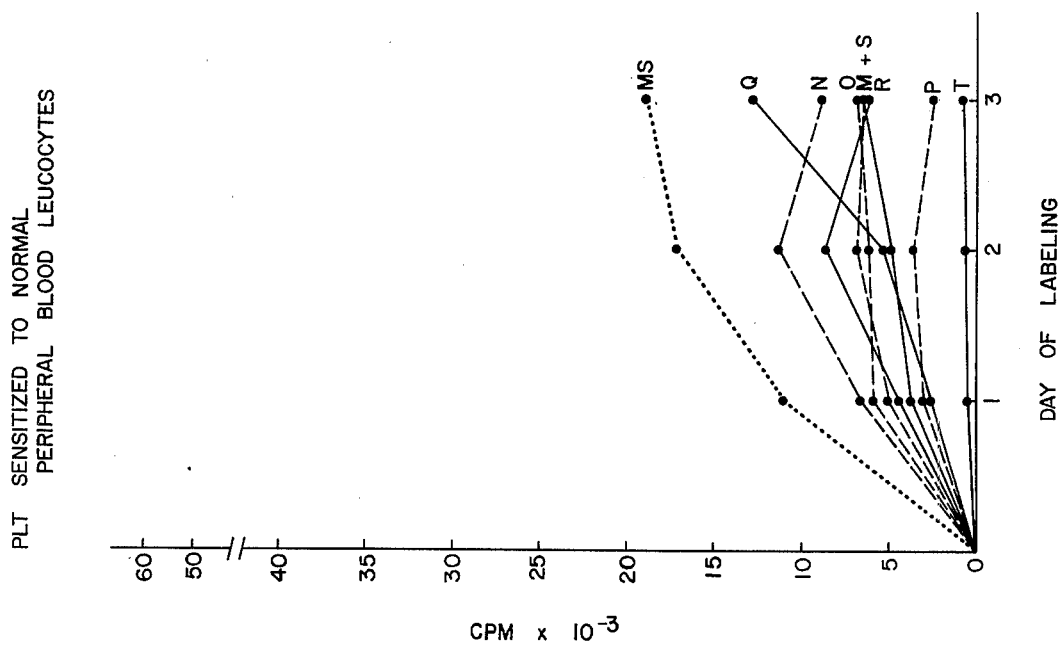

The results shown in FIGS. 1C and 1D are from an experiment in which primary MLC sensitization was accomplished with peripheral blood lymphocytes of a DW2 homozygous typing cell (MS) (see Reinsmoen et al, Histocompatibility Testing, ed. Kissmeyer - Neilsen, F., pp. 459-463, Munksgaard, Copenhagen (1975)) (FIG. 1C) and with the lymphoblastoid cell line of that homozygous typing cell (FIG. 1D). Restimulation of these PLT cells was done with normal peripheral blood lymphocytes of the reference cell donor, four unrelated individuals (M, N, O and P) whose cells are positive for DW2 by homozygous typing cell testing) and four unrelated test cells (individuals Q, R, S and T) whose cells are negative for DW2.

Although the Figures present results for later time points, PLT is usually assayed before 48 hours, i.e., before the appearance of secondary inhibitory effects (as can be seen, for example, with restimulating cells E and F in FIG. 1A). Data comparisons would normally be made when PLT cultures were labelled at 24 hours and read 16 hours later.

In FIGS. 1A - 1D the dotted line represents the results obtained with the reference cell, the dashed line the results obtained with test cells carrying the DW haplotype and the solid line results obtained with cells not carrying the sensitizing DW haplotype.

The reference restimulating cell gives maximal or near maximal restimulation, the other test restimulating cells that carry the HLA-D haplotype of the reference cell on the average give higher restimulation than test cells that do not carry the D haplotype.

Referring specifically to the Figures it is apparent that the results from using the PLT cells in FIGS. 1A and 1B are very similar: only test cell H restimulates more than the test cell (KH). Test cells F, E and G show decreasing amounts of restimulation. All individuals not carrying the DW haplotype of KH restimulate the least. Although the data shown in FIG. 1C does not give very good discrimination, it does, in fact, parallel that shown in FIG. 1D, i.e, the reference cell restimulates the most in both cases, individuals N, O and M (which carry the sensitizing DW haplotype) show decreased amounts or restimulation; cell of individual P which also carry the sensitizing haplotype by homozygous typing cell testing, restimulate less than some of the test cells not carrying that haplotype in FIG. 1C and are also relatively low in FIG. 1D.

It is apparent from the data presented that PLT cells made against lymphoblastoid cell lines give results very similar to those sensitized to normal cells. It is to be understood that the testing (typing) using the PLT cells that have been generated against specific HLA-D antigens on the lymphoblastoid cell lines, will be done using normal peripheral blood lymphocytes from the individual to be tested.

If desired, PLT cells prepared by the method of this invention can be conveniently frozen for future use in accordance with the following procedure.

FREEZING PLT CELLS

Freezing methods are those used for fresh lymphocytes. Freezing medium consists of 70% medium or PBS, 20% heat-in-activated and filtered (0.45m milipore) pooled human serum, and 10% dimethyl sulfoxide DMSO). Cells are suspended in cold freezing medium (4° C), distributed into Nunc plastic freezing vials in convenient numbers (about 6–20 × $10^6$ per vial), and placed in a very thin cardboard box or an open container into a −80° C freezer overnight. Later, vials may be transferred to liquid nitrogen tanks for long-term storage. (PBS = phosphate buffered saline).

Before use, cells are thawed rapidly by shaking vials in a 37° C water bath until ice is just melted, diluted 3-fold with cold PBS (4° C), and centrifuged gently (6 minutes, 70 g) to pellet cells. Pellet is resuspended in plasma-supplemented medium for counting and culturing.

Fresh PLT cells prepared as described above, as well as those preserved by the above freezing method, have been found to give quantitatively similar results, it is possible to prepare typing trays that contain frozen PLT cells defining many different LD antigens. The LD type of any person could be rapidly determined by stimulation of the different PLT cells in this panel.

The ability to identify LD antigens may be important in other ways besides its obvious application to transplant matching. LD antigens are controlled by the same region of the MHC that controls the magnitude of immune responses to certain specific antigens. Moreover, the LD region has been associated with susceptibility to oncogenic viral infections in the mouse, and certain LD antigens have been associated with disease of immune etiology in man. Thus PLT may be an important criterion for diagnosing human disease, as well as a specific probe allowing greater understanding of the function and genetic fine structure of the MHC in man and in other species.

It will be evident to those skilled in the art that the aforedescribed procedures and the present invention will also be applicable to cells with different D-locus specifications.

In addition, it seems reasonable to presume that the PLT approach will be usable in the typing of other than HLA-D antigens for diagnostic purposes.

Having thus described the invention, what is claimed is:

1. A method for preparation of a reagent for lymphocyte-defined typing of human leukocyte antigens which comprises incubating in vitro purified blood leukocytes with human cells selected from lymphoblastoid cell lines from homozygous typing cells, other cells homozygous for HLA-D, or other continuous line cells, and recovering the leukocytes from the incubation medium.

2. A method according to claim 1 in which the leukocytes recovered from the incubation medium contains lymphocytes that have been primed to recognize given HLA-D region antigens.

3. A method according to claim 2 in which the incubation is carried out essentially to completion of the proliferative response.

4. A method according to claim 2 in which the incubation is carried out for a period of from about 9 to about 14 days.

5. A method according to claim 4 in which the incubation is terminated after 10 days.

6. A reagent for lymphocyte defined typing of human leukocyte antigens produced by the method of claim 1.

7. A reagent according to claim 6 which contains lymphocytes that have been primed to recognize a given HLA-D region antigen(s).

8. A method for assaying for antigenic compatibility comprising measuring the proliferative responsive of the primed lymphocytes of claim 7 to antigens of restimulating cells of a third person.

9. A method for typing human leukocyte antigens comprising incubating in vitro the reagent of claim 6 with purified human block leukocytes obtained from a third person, measuring the response of the recovered leukocytes through the uptake by the responding leukocytes of tritiated thymidine or tritiated uridine added to the incubating mixture, said measurement defining the antigens present in the third person.

* * * * *